United States Patent
Xu et al.

(10) Patent No.: US 12,420,070 B2
(45) Date of Patent: Sep. 23, 2025

(54) DOUBLE-BALLOON THROMBOLYSIS AND THROMBECTOMY DEVICE

(71) Applicant: Beijing Taijieweiye Technology Co., Ltd, Beijing (CN)

(72) Inventors: Yongsong Xu, Beijing (CN); Qi Guo, Beijing (CN); Zhimei Liao, Beijing (CN); Rui Wang, Beijing (CN); Hang Tang, Beijing (CN); Jian Wu, Beijing (CN)

(73) Assignee: Beijing Taijieweiye Technology Co., Ltd, Beijing (CN)

( * ) Notice: Subject to any disclaimer, the term of this patent is extended or adjusted under 35 U.S.C. 154(b) by 118 days.

(21) Appl. No.: 18/558,101

(22) PCT Filed: Nov. 2, 2021

(86) PCT No.: PCT/CN2021/128040
§ 371 (c)(1),
(2) Date: Oct. 30, 2023

(87) PCT Pub. No.: WO2022/257343
PCT Pub. Date: Dec. 15, 2022

(65) Prior Publication Data
US 2024/0216655 A1    Jul. 4, 2024

(30) Foreign Application Priority Data
Jun. 9, 2021  (CN) .......................... 202110645075.5

(51) Int. Cl.
*A61M 25/10*  (2013.01)
*A61B 17/22*  (2006.01)

(52) U.S. Cl.
CPC ......... *A61M 25/1011* (2013.01); *A61B 17/22* (2013.01); *A61B 2017/22054* (2013.01); *A61B 2017/22067* (2013.01)

(58) Field of Classification Search
CPC ...... A61M 25/1011; A61M 2025/1013; A61M 2025/1015; A61M 2025/105; A61B 2017/22054
See application file for complete search history.

(56) References Cited

U.S. PATENT DOCUMENTS

| | | | |
|---|---|---|---|
| 2002/0016565 A1* | 2/2002 | Zadno-Azizi | A61M 25/0054 604/101.03 |
| 2002/0052638 A1* | 5/2002 | Zadno-Azizi | A61B 17/12109 623/1.2 |

(Continued)

FOREIGN PATENT DOCUMENTS

| | | |
|---|---|---|
| CN | 102698354 A | 10/2012 |
| CN | 203469211 | 3/2014 |

(Continued)

OTHER PUBLICATIONS

International Search Report for Application No. PCT/CN2021/128040 dated Feb. 28, 2022, 2 pages.

(Continued)

*Primary Examiner* — Katherine H Schwiker
(74) *Attorney, Agent, or Firm* — TraskBritt

(57) ABSTRACT

A double-balloon thrombolysis and thrombectomy device, comprising a catheter, an access sheath, and a hemostasis valve. The catheter comprises a base, a body, a first balloon, and a second balloon, the first balloon and the second balloon are sleeved over the body, the first balloon is located at a distal end of the body, and the second balloon is located at the proximal end of the first balloon; the base is connected to the proximal end of the body, and comprises a main connection port, a first connection port and a second connection port; the first balloon is connected to the first connection port, and the second balloon is connected to the second connection port; the surface of the second balloon is provided with a plurality of micropores; and the access (Continued)

sheath is sleeved over the catheter body, and connected to the catheter body through the hemostasis valve.

6 Claims, 1 Drawing Sheet

(56) References Cited

U.S. PATENT DOCUMENTS

2010/0280451 A1* 11/2010 Teeslink ............ A61M 25/1011
                                                          604/99.04
2010/0305678 A1   12/2010 Alaswad

FOREIGN PATENT DOCUMENTS

| CN | 203852722    | 10/2014 |              |
|----|--------------|---------|--------------|
| CN | 108114361 A  | 6/2018  |              |
| CN | 113398439 A  | 9/2021  |              |
| WO | WO-0119445 A1 * | 3/2001 | .......... A61M 25/104 |

OTHER PUBLICATIONS

International Written Opinion for Application No. PCT/CN2021/128040 dated Feb. 28, 2022, 5 pages.
International Search Report for International Application No. PCT/CN2021/128040, mailed Feb. 28, 2022, 06 pages.
International Written Opinion for International Application No. PCT/CN2021/128040, mailed Feb. 28, 2022, 05 pages.

* cited by examiner

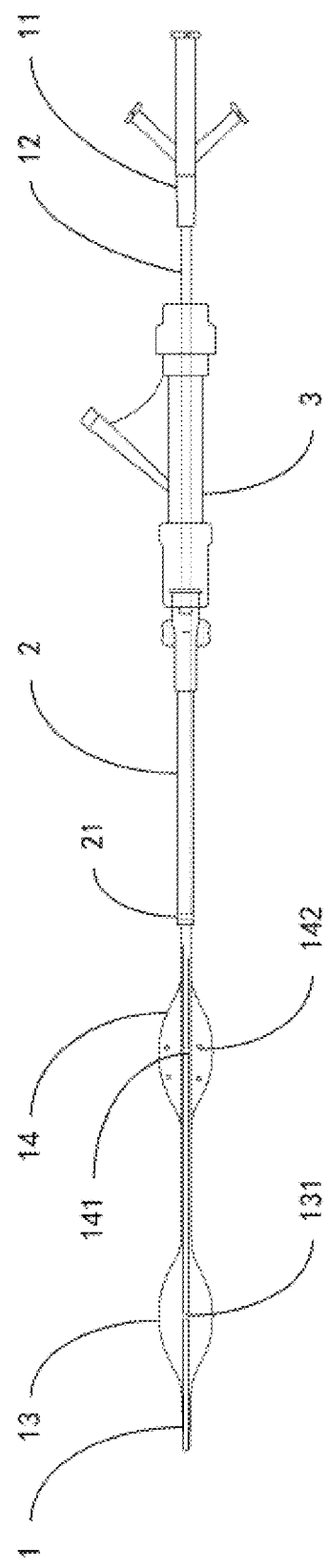

DOUBLE-BALLOON THROMBOLYSIS AND THROMBECTOMY DEVICE

CROSS-REFERENCE TO RELATED APPLICATIONS

This application is a national phase entry under 35 U.S.C. § 371 of International Patent Application PCT/CN2021/128040, filed Nov. 2, 2021, designating the United States of America and published as International Patent Publication WO 2022/257343 A1 on Dec. 15, 2022, which claims priority under Article 8 of the Patent Cooperation Treaty to Chinese Patent Application Serial No. 202110645075.5, filed in the China Patent Office on Jun. 9, 2021, and titled "DOUBLE-BALLOON THROMBOLYSIS AND THROMBECTOMY DEVICE."

TECHNICAL FIELD

The present disclosure relates to the field of medical devices and, in particular, to a double-balloon thrombolysis and thrombectomy device.

BACKGROUND

At present, there are two major therapies for acute ischemic stroke. One is a simple drug thrombolysis therapy, by which a thrombolytic drug is typically injected intravenously. However, once intravenous thrombolysis fails or is far from the expectation, femoral artery puncture needs to be carried out to thus carry out stent thrombectomy or vascular aspiration, which increases wound sites during the surgical operation and prolongs the treatment time window, resulting in a poor clinical prognosis effect, even though the latter operation is successful. The other is simple stent thrombectomy or vascular aspiration, both of which face the problem of thrombus escape. Moreover, a variety of distal end protectors (filter screen braided type or metal skeleton type polyurethane models) available on the market at present are largely for use in large blood vessels such as carotid artery. However, the intracranial vascular stroke generally occurs in M1 or M2 or even a more distal end in cerebral arteries, and the traditional thrombus protector cannot provide proper protection directly.

BRIEF SUMMARY

The present disclosure is to provide a double-balloon thrombolysis and thrombectomy device, which uses a double-balloon catheter to inject normal saline into a first balloon at a distal end of the double-balloon catheter to expand the first balloon to completely fit an inner wall of a blood vessel so as to block a blood flow at a distal end and prevent the thrombus from escaping; a thrombolytic drug is injected into a second balloon, from which the thrombolytic drug is released by means of micropores in the surface of the second balloon to the blood vessel for thrombosis; and after the thrombosis is completed, a negative pressure is applied to a lumen of an access sheath by means of a Y-type hemostasis valve to suck away the dissolved thrombus, which greatly shortens the surgical operation time window, improves the clinical prognosis effect, and provides distal-end protection throughout the process to prevent the thrombus from escaping, thereby making the surgical operation safer.

The present disclosure provides a double-balloon thrombolysis and thrombectomy device, including:

a double-balloon catheter comprising a three-way catheter base, a catheter body, a first balloon and a second balloon, wherein a distal end of the three-way catheter base is connected to a proximal end of the catheter body, the first balloon and the second balloon are respectively sleeved over the catheter body, the first balloon is located at a distal end of the catheter body, the second balloon is located at a proximal end of the first balloon, the three-way catheter base comprises a main connection port, a first connection port and a second connection port, the catheter body comprises a catheter body lumen, a first lumen passage and a second lumen passage, the first lumen passage and the second lumen passage are respectively located on an inner wall of the catheter body lumen, the first balloon and the first connection port are connected by means of the first lumen passage, the second balloon and the second connection port are connected by means of the second lumen passage, the catheter lumen and the main connection port are connected, and a plurality of micropores are uniformly distributed in a surface of the second balloon;

an access sheath sleeved over the catheter body, wherein a distal end of the access sheath is located at a proximal end of the second balloon; and a Y-type hemostasis valve sleeved over the catheter body, wherein a proximal end of the access sheath is fixedly connected to the catheter body by means of the Y-type hemostasis valve, wherein a guide wire passing through the catheter body lumen pushes the double-balloon catheter into a blood vessel to push the first balloon to a distal end of a vascular thrombosis site, such that the second balloon is embedded into the vascular thrombosis site; normal saline is injected into the first balloon by means of the first connection port to expand the first balloon to completely fit an inner wall of the blood vessel so as to prevent thrombus from escaping; a thrombolytic drug is injected into the second balloon by means of the second connection port to create a pressure inside the second balloon to allow the micropores in the surface of the second balloon to open, such that the thrombolytic drug is released by means of the micropores to the vascular thrombosis site for thrombolysis; and a negative pressure is applied to a lumen of the access sheath by means of the Y-type hemostasis valve to suck away small broken thrombus.

Preferably, the catheter body in the first balloon is provided with a first positioning mark; the catheter body in the second balloon is provided with a second positioning mark, and the catheter body at the distal end of the access sheath is provided with a third positioning mark.

Preferably, the micropores in the surface of the second balloon are pressure-response type micropores, with a number ranging from 2 to 10 and a diameter of 20-100 microns.

Preferably, a distance between the first balloon and the second balloon is 1-3 cm;

the first balloon is a compliant balloon and is made of silicone or thermoplastic polyurethane; and the second balloon is a compliant or semi-compliant balloon and is made of silicone, thermoplastic polyurethane, or a block polyether phthalamine polymer.

Preferably, the catheter body has an outer diameter of 1.8-3.2 F, an inner diameter of 0.015-0.027 inch, and a length of 140-160 cm.

Preferably, the access sheath has an outer diameter of 5-8 F, an inner diameter of 0.058-0.088 inch, and a length of 90-120 cm.

The embodiment of the present disclosure provides a double-balloon thrombolysis and thrombectomy device, by which the double-balloon catheter is used to inject normal saline into the first balloon at the distal end of the double-balloon catheter to expand the first balloon to completely fit an inner wall of a blood vessel so as to block a blood flow at a distal end and prevent the thrombus from escaping; a thrombolytic drug is injected into the second balloon, from which the thrombolytic drug is released by means of micropores in the surface of the second balloon to the blood vessel for thrombosis; and after the thrombosis is completed, a negative pressure is applied to the lumen of the access sheath by means of the Y-type hemostasis valve to suck away the dissolved thrombus, which greatly shortens the surgical operation time window, improves the clinical prognosis effect, and provides distal-end protection throughout the process to prevent the thrombus from escaping, thereby making the surgical operation safer.

BRIEF DESCRIPTION OF THE DRAWINGS

FIG. 1 is a schematic structural diagram of a double-balloon thrombolysis and thrombectomy device according to an embodiment of the present disclosure.

DETAILED DESCRIPTION

The technical solutions of the present disclosure will be further described in details below in combination with the accompanying drawings and embodiments.

The embodiment of the present disclosure provides a double-balloon thrombolysis and thrombectomy device, which uses a double-balloon catheter to inject normal saline into a first balloon at a distal end of the double-balloon catheter to expand the first balloon to completely fit an inner wall of a blood vessel so as to block a blood flow at a distal end and prevent the thrombus from escaping; a thrombolytic drug is injected into the second balloon, from which the thrombolytic drug is released by means of micropores in the surface of the second balloon to the blood vessel for thrombosis; and after the thrombosis is completed, a negative pressure is applied to a lumen of an access sheath by means of a Y-type hemostasis valve to suck away the dissolved thrombus, which greatly shortens the surgical operation time window, improves the clinical prognosis effect, and provides distal-end protection throughout the process to prevent the thrombus from escaping, thereby making the surgical operation safer.

FIG. 1 is a schematic structural diagram of a double-balloon thrombolysis and thrombectomy device according to an embodiment of the present disclosure. As shown in FIG. 1, the double-balloon thrombolysis and thrombectomy device includes a double-balloon catheter 1, an access sheath 2 and a Y-type hemostasis valve 3.

The double-balloon thrombolysis and thrombectomy device provided by the embodiment of the present disclosure is applicable to intravascular local thrombolysis treatment, and can be used to complete the thrombolysis and thrombectomy operation within a short time.

The double-balloon catheter 1 is located on a lumen of the access sheath 2, and the two can be moved or pushed relative to each other; and the Y-type hemostasis valve 3 is configured to fixedly connect a proximal end of the access sheath 2 and the double-balloon catheter 1 into a whole.

The access sheath 2 has an outer diameter of 5-8 F ("F" is a unit of French metric system for the diameter of medical catheters, 1 F≈0.33 mm), an inner diameter of 0.058-0.088 inch, and a length of 90-120 cm.

The double-balloon catheter 1 includes a three-way catheter base 11, a catheter body 12, a first balloon 13, and a second balloon 14. A distal end of the three-way catheter base 11 is connected to a proximal end of the catheter body 12. The first balloon 13 and the second balloon 14 are respectively sleeved over the catheter body 12; the first balloon 13 is located at a distal end of the catheter body 12; the second balloon 14 is located at a proximal end of the first balloon 13; and a distance between the first balloon 13 and the second balloon 14 is 1-3 cm.

The catheter body 12 of the double-balloon catheter 1 has an outer diameter of 1.8-3.2 F, an inner diameter of 0.015-0.027 inch, and a length of 140-160 cm.

The three-way catheter base 11 has a main connection port, a first connection port, and a second connection port, and the catheter body 12 has a catheter body lumen, a first lumen passage, and a second lumen passage. The first lumen passage and the second lumen passage are respectively located on an inner wall of the catheter body lumen; a proximal end of the catheter body lumen is communicated to the main connection port of the three-way catheter base 11; a proximal end of the first lumen passage is communicated to the first connection port of the three-way catheter base 11; a distal end of the first lumen passage is communicated to a lumen of the first balloon 13; a proximal end of the second lumen passage is communicated to the second connection port of the three-way catheter base 11; and a distal end of the second lumen passage is communicated to a lumen of the second balloon 14.

The first balloon 13 is a compliant balloon and is made of silicone, thermoplastic polyurethane or other polymer materials with good elasticity. The diameter of the first balloon 13 can significantly increase with the increase of spreading pressure. The first balloon 13 is configured to rapidly expand and fit an inner wall of a blood vessel at a distal end of a vascular thrombosis site to temporarily block the blood vessel at the distal end, thereby preventing the small broken thrombosis from escaping to the distal end during a surgical operation.

The second balloon 14 is a compliant or semi-compliant balloon and is made of silicone, thermoplastic polyurethane, a block polyether phthalamine polymer, or other polymer materials. The second balloon 14 is configured to provide a thrombolytic drug for local thrombolytic treatment on the thrombosis at the vascular thrombosis site. A plurality of micropores 142 are uniformly distributed in the surface of the body of the second balloon 14. The micropores 142 have a diameter of 20-100 microns, with a number ranging from 2 to 10; the micropores 142 are pressure-response type micropores, which are closed in an unpressured state, i.e., a state where no thrombolytic drug is injected to the interior of the second balloon 14, thereby preventing air entering the lumen of the second balloon 14 prior to use.

In an unpressured state, the diameter of each of the first and second balloons 13 and 14 is the same as or slightly larger than the outer diameter of the catheter body 12, without any influence on the delivery of the double-balloon catheter 1 in the access sheath 2.

The catheter body 12 is provided with a first positioning mark 131 and a second positioning mark 141. The first positioning mark 131 is disposed on the catheter body in the first balloon 13, and the second positioning mark 141 is disposed on the catheter body in the second balloon 14. The distal end of the access sheath 2 is further provided with a third positioning mark 21. These positioning marks are for the purpose of observation during the surgical operation.

The embodiment of the present disclosure concretely works as follows.

During the surgical operation, a guide wire passes through the main connection port of the three-way catheter base 11 and enters the catheter body lumen of the catheter body 12 to push the double-balloon catheter 1 into a blood vessel, until the first balloon 13 passes through a vascular thrombosis site to reach a distal end of the vascular thrombosis site and the second balloon 14 is exactly embedded into the vascular thrombosis site. Normal saline is injected into the first balloon 13 by means of the first connection port of the three-way catheter base 11 to expand the first balloon 13 to completely fit an inner wall of the blood vessel, so as to temporarily block the blood flow at the distal end and prevent the small broken thrombus from escaping to the distal end. Then, a thrombolytic drug is injected into the second balloon 14 by means of the second connection port of the three-way catheter base 11, so as to expand the second balloon 14 outwards to mechanically extrude clumpy thrombus, thereby breaking the thrombus into small pieces; and meanwhile, due to the pressure inside the second balloon 14, the pressure-response type micropores in the surface of the second balloon 14 are opened to release a thrombus softening or thrombolysis drug into the blood vessel from the interior of the second balloon 14, making the thrombus easier to suck away. After about 5-10 minutes, the drug release from the second balloon 14 is completed, the second balloon 14 restores to the initial contraction state, and here, a negative pressure is applied to the lumen of the access sheath 2 by means of the connection port on the Y-type hemostasis valve 3 to perform continuous sucking for 3-30 seconds, whereby the small broken thrombus is sucked away to completely smoothen the blood vessel.

With respect to the prior art, the embodiment of the present disclosure provides a double-balloon thrombolysis and thrombectomy device, by which the double-balloon catheter is used to inject normal saline into the first balloon at the distal end of the double-balloon catheter to expand the first balloon to completely fit an inner wall of a blood vessel so as to block a blood flow at a distal end and prevent the thrombus from escaping; a thrombolytic drug is injected into the second balloon, from which the thrombolytic drug is released by means of micropores in the surface of the second balloon to the blood vessel for thrombosis; and after the thrombosis is completed, a negative pressure is applied to the lumen of the access sheath by means of the Y-type hemostasis valve to suck away the dissolved thrombus, which greatly shortens the surgical operation time window, improves the clinical prognosis effect, and provides distal-end protection throughout the process to prevent the thrombus from escaping, thereby making the surgical operation safer.

The objects, technical solutions and advantageous effects of the present disclosure are further illustrated in detail with the specific embodiments described above. It should be understood that the description above only involves the specific embodiments of the present disclosure and is not intended to limit the protection scope of the present disclosure. Any modifications, equivalent substitutions, improvements and the like made within the spirit and principle of the present disclosure shall be construed as being included within the protection scope of the present disclosure.

What is claimed is:

1. A double-balloon thrombolysis and thrombectomy device, comprising:
a double-balloon catheter comprising a three-way catheter base, a catheter body, a first balloon and a second balloon, wherein a distal end of the three-way catheter base is connected to a proximal end of the catheter body, the first balloon and the second balloon are respectively sleeved over the catheter body, the first balloon is located at a distal end of the catheter body, the second balloon is located at a proximal end of the first balloon, the three-way catheter base comprises a main connection port, a first connection port and a second connection port, the catheter body comprises a catheter body lumen, a first lumen passage and a second lumen passage, the first lumen passage and the second lumen passage are respectively located on an inner wall of the catheter body lumen, the first balloon and the first connection port are connected through the first lumen passage, the second balloon and the second connection port are connected through the second lumen passage, the catheter body lumen and the main connection port are connected, and a plurality of micropores are uniformly distributed in a surface of the second balloon;
an access sheath sleeved over the catheter body, wherein a distal end of the access sheath is located at a proximal end of the second balloon; and
a Y-type hemostasis valve sleeved over the catheter body, wherein a proximal end of the access sheath is fixedly connected to the catheter body through the Y-type hemostasis valve,
wherein a guide wire passing through the catheter body lumen pushes the double-balloon catheter into a blood vessel to push the first balloon to a distal end of a vascular thrombosis site, such that the second balloon is embedded into the vascular thrombosis site; normal saline is injected into the first balloon through the first connection port to expand the first balloon to completely fit an inner wall of the blood vessel so as to prevent thrombus from escaping; a thrombolytic drug is injected into the second balloon through the second connection port to create a pressure inside the second balloon to allow the micropores in the surface of the second balloon to open, such that the thrombolytic drug is released through the micropores to the vascular thrombosis site for thrombolysis; and a negative pressure is applied to a lumen of the access sheath through the Y-type hemostasis valve to suck away small broken thrombus.

2. The double-balloon thrombolysis and thrombectomy device of claim 1, wherein the catheter body in the first balloon is provided with a first positioning mark, the catheter body in the second balloon is provided with a second positioning mark, and the catheter body at the distal end of the access sheath is provided with a third positioning mark.

3. The double-balloon thrombolysis and thrombectomy device of claim 1, wherein the micropores in the surface of the second balloon are pressure-response type micropores, with a number ranging from 2 to 10 and a diameter of 20-100 microns.

4. The double-balloon thrombolysis and thrombectomy device of claim 1, wherein a distance between the first balloon and the second balloon is 1-3 cm;
the first balloon is a compliant balloon and is made of silicone or thermoplastic polyurethane; and
the second balloon is a compliant or semi-compliant balloon and is made of silicone, thermoplastic polyurethane, or a block polyether phthalamine polymer.

5. The double-balloon thrombolysis and thrombectomy device of claim 1, wherein the catheter body has an outer diameter of 1.8-3.2 F, an inner diameter of 0.015-0.027 inch, and a length of 140-160 cm.

6. The double-balloon thrombolysis and thrombectomy device of claim 1, wherein the access sheath has an outer diameter of 5-8 F, an inner diameter of 0.058-0.088 inch, and a length of 90-120 cm.

\* \* \* \* \*